(12) United States Patent
Lenz

(10) Patent No.: US 8,318,426 B2
(45) Date of Patent: *Nov. 27, 2012

(54) POLYMORPHISMS IN VOLTAGE-GATED SODIUM CHANNEL ALPHA 1-SUBUNIT AS MARKERS FOR THERAPY SELECTION

(75) Inventor: Heinz-Josef Lenz, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 12/732,985

(22) Filed: Mar. 26, 2010

(65) Prior Publication Data

US 2010/0216826 A1    Aug. 26, 2010

Related U.S. Application Data

(63) Continuation of application No. 11/681,670, filed on Mar. 2, 2007, now Pat. No. 7,727,724.

(60) Provisional application No. 60/778,670, filed on Mar. 3, 2006.

(51) Int. Cl.
*C12Q 1/68* (2006.01)
(52) U.S. Cl. ...................................................... 435/6.1
(58) Field of Classification Search .................. None
See application file for complete search history.

(56) References Cited

U.S. PATENT DOCUMENTS

| | | | |
|---|---|---|---|
| 6,716,581 | B2 | 4/2004 | Lenz et al. |
| 2004/0067519 | A1 | 4/2004 | Lenz et al. |
| 2006/0094012 | A1 | 5/2006 | Lenz et al. |
| 2006/0115827 | A1 | 6/2006 | Lenz |
| 2007/0207486 | A1 | 9/2007 | Lenz |
| 2007/0218487 | A1 | 9/2007 | Lenz |
| 2008/0286789 | A1 | 11/2008 | Lenz et al. |
| 2009/0181016 | A1 | 7/2009 | Lenz |

FOREIGN PATENT DOCUMENTS

| | | |
|---|---|---|
| WO | WO 2007/064957 | 6/2007 |
| WO | WO 2008/088854 | 7/2008 |
| WO | WO 2008/088855 | 7/2008 |
| WO | WO 2008/088860 | 7/2008 |
| WO | WO 2008/088861 | 7/2008 |
| WO | WO 2008/088876 | 7/2008 |
| WO | WO 2008/088893 | 7/2008 |
| WO | WO 2008/089465 | 7/2008 |
| WO | WO 2008/144512 | 11/2008 |
| WO | WO 2009/151448 | 12/2009 |

OTHER PUBLICATIONS

Tockman et al (Cancer Res., 1992, 52:2711s-2718s).*
Escayg et al (Am J Hum Genet, 2001, 68: 866-873).*
U.S. Appl. No. 09/715,764, filed Nov. 15, 2000, Lenz.
Douglass et al. (1986) "Survival after Postoperative Combination Treatment of Rectal Cancer," *N. Eng. J. Med.* 315:1294-1295.

Douillard et al. (2000) "Irinotecan combined with fluorouracil compared with fluorouracil alone as first-line treatment for metastatic colorectal cancer: a multicentre randomized trial" *Lancet* 355:1041-1047.
Escayg et al. (2001) "A novel SCN1A mutation associated with generalized epilepsy with febrile seizures plus-and prevalence of variants in patients with epilepsy" *Am. J. Hum. Genet.* 68:866-873.
Fraser et al. (2005) "Voltage-gated sodium channels expression and potentiation of human breast cancer metastasis" *Clin. Cancer Res.* 11:5381-5389.
Gaber et al. (2003) "Retrospective analysis of 5-FU/LV/CPT-11 2 weeks on/1 week off (IFL2), a pilot study," Proc ASCO 22:1515.
Goldberg et al. (2004) "A Randomized Controlled Trial of Fluorouracil Plus Leucovorin, Irinotecan, and Oxaliplatin Combinations in Patients with Previously Untreated Metastatic Colorectal Cancer" *J. Clin. Oncol.* 22(1):23-30.
Grolleau et al. (2001) "A Possible Explanation for a Neurotoxic Effect of the Anticancer Agent Oxaliplatin on Neuronal Voltage-Gated Sodium Channels," *J. Neurophysiology* 85:2293-2297.
Heidelberger et al. (1957) "Fluorinated pyrimidines: A new class of tumor inhibitor compounds" *Nature* 179:663-666.
Iqbal & Lenz (2001) "Determinants of prognosis and response to therapy in colorectal cancer," *Curr. Oncol. Rep.* 3(2)102-108.
Iqbal et al. (2003) "Targeted therapy and pharmacogenomic programs" *Cancer* 97:2076-2082.
Iqbal et al. (2003) "Molecular predictors of treatment and outcome in colorectal cancer," *Curr Gastroenterol Rep* 5(5):399-405.
Iqbal et al. (2004) "Tailored chemotherapy for colorectal cancer: a new approach to therapy" *Cancer Invest.* 22(5):762-773.
Iqbal et al. (2005) "Individualized Chemotherapy Based on Genetic and Genomic Profiling," *Curr Colorectal Cancer Rep* 1(2): 91-102.
Jemal et al. (2005) "Cancer Statistics, 2005," *Cancer J. Clin.* 55(1):10-30.
Kastan (1991) "Participation of p53 Protein in the Cellular Response to DNA Damage," *Cancer Res.* 51:6304-6311.
Lenz (2002) "Pharmacogenetic determinants of clinical outcome and toxicity in colon cancer," *Eur J Cancer* 38(Suppl. 7):S68 #212.
Lenz (2003) "Pharmacogenomics in colorectal cancer," *Semin Oncol.* 30(4 Suppl 15):47-53.
Lenz et al. (1997) "Molecular markers as indicators of response and outcome in primary gastric cancer" *Prog Gastric Cancer Res* 2:1295-1300.
Lenz et al. (2002) A multivariate analysis of genetic markers for clinical response to 5-FU/oxaliplatin chemotherapy in advanced colorectal cancer. Proc ASCO 21:513.
Lenz (2004) "The Use and Development of Germline Polymorphisms in Clinical Oncology," *J. Clin. Oncol.* 22(13):2519-2521.

(Continued)

*Primary Examiner* — Sean Aeder
(74) *Attorney, Agent, or Firm* — Foley & Lardner LLP; Antoinette F. Konski; Alex Y. Nie

(57) ABSTRACT

A method for determining whether a patient in need thereof will respond to chemotherapy by screening a suitable sample isolated from the patient for a pre-selected polymorphism present in the VGSC gene.

7 Claims, No Drawings

OTHER PUBLICATIONS

Levine (1992) "The p53 Tumor-Suppressor Gene," *N. Engl. J. Med.* 326:1350-1352.

Llombart-Bosch et al. (eds.) *New Trends in Cancer for the 21st Century 2nd Edition, Series: Advances in Experimental Medicine and Biology*, 2006, vol. 587, Chapter 18: Pharmacogenomics and Colorectal Cancer, pp. 211-231, Springer.

Machover et al. (1996) "Two consecutive phase II studies of oxaliplatin (L-OHP) for treatment of patients with advanced colorectal carcinoma who were resistant to previous treatment with fluoropyrimidines," *Ann. Oncol.* 7(1):95-98.

Moertel (1994) "Chemotherapy for colorectal cancer" *N. Engl. J. Med.* 330:1136-1142.

Nagashima et al. (2006) "Polymorphism in sodium-channel alpha 1-subunit (SCN1A) predicts response, TTP, survival, and toxicity in patients with metastatic colorectal cancer treated with 5-FU/oxaliplatin" *Proc ASCO* 24:3533: Abstract.

Nagashima et al. (2006) "Polymorphism in sodium-channel alpha 1-subunit (SCN1A) predicts response, TTP, survival, and toxicity in patients with metastatic colorectal cancer treated with 5-FU/oxaliplatin" *Proc ASCO* 24:3533: Poster: [Retrieved online on Jul. 21,2008 at the following: http://www.asco.org/ASCO/Abstracts+%26+Virtual+Meeting/Abstracts?&vmview=abst_detail_view&confID=40&abstractID=31130].

Nunez (1996) "Relationship between DNA damage, rejoining and cell killing by radiation in mammalian cells," *Rad. Onc.* 39:155-165.

Park et al. (2006) "Determinants of chemosensitivity in gastric cancer," *Curr. Opin. Pharma.* 6(4):337-344.

Park et al. (2003) "Tailoring chemotherapy in advanced colorectal cancer," Curr Opin Pharmacol 3(4):378-385.

Rougier & Lepre (2005) "Metastatic Colorectal Cancer: First- and Second-Line Treatment in 2005," *Semin. Oncol.* 32(6 Suppl. 8):15-20.

Saltz et al. (2000) "Irinotecan plus fluoruracil and leucovorin for metastatic colorectal cancer" *N. Engl. J. Med.* 343(13):905-914.

Stoehlmacher & Lenz (2003) "Implications of genetic testing in the management of colorectal cancer," *Am. J. Pharmacogenomics* 3(2):73-88.

Stoehlmacher et al. (2004) "A multivariate analysis of genomic polymorphisms: prediction of clinical outcome to 5-FU/oxaliplatin combination chemotherapy in refractory colorectal cancer," *Br. J. Cancer* 91(2):344-54.

Vallboehmer et al. (2006) "Molecular Determinants of Irinotecan Efficacy," *International Journal of Cancer* 119(10):2435-42. Nov. 15.

Viguier et al. (2005) "ERCC1 codon 118 polymorphism is a predictive factor for the tumor response to oxaliplatin/5-fluorouracil combination chemotherapy in patients with advanced colorectal cancer" *Clin. Cancer Res.* 11:6212-6217.

Yan & Beckman (2005) "Pharmacogenetics and pharmacogenomics in oncology therapeutic antibody development," *Biotechniques* 39:565-568.

Yanagisawa et al. (1998) "Increased expression of human DNA repair genes, XRCC1, XRCC3 and RAD51, in radioresistant human KB carcinoma cell line N10," *Oral Oncol.* 34:524-528.

Yang et al. (2005) "Molecular prognostic factors of irinotecan efficacy," *Proc ASCO* 23:3621.

Yun et al. (2004) "Molecular profiling predicts clinical outcome in patients with metastatic colorectal cancer treated with 5-FU/oxaliplatin," *Proc ASCO* 23:3519.

Zhang et al. (2006) "Cyclin D1 and epidermal growth factor polymorphisms associated with survival in patients with advanced colorectal cancer treated with Cetuximab," *Pharma. and Genomics* 16(7):475-483.

\* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 1
tgcacaaagg agtagcttat g                                              21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtcaagatc tttcccaatt tcag                                           24
```

POLYMORPHISMS IN VOLTAGE-GATED SODIUM CHANNEL ALPHA 1-SUBUNIT AS MARKERS FOR THERAPY SELECTION

CROSS-REFERENCE TO RELATED APPLICATIONS

This application is a continuation of U.S. patent application Ser. No. 11/681,670, filed Mar. 2, 2007, now U.S. Pat. No. 7,727,724, which claims the benefit under 35 U.S.C. §119(e) to U.S. Provisional Patent Application No. 60/778,670, filed Mar. 3, 2006, the contents of each of which are incorporated by reference into the present disclosure.

STATEMENT OF GOVERNMENT SUPPORT

This invention was made with government support under Contract No. CA082754 awarded by the National Institutes of Health. The government has certain rights in the invention.

FIELD OF THE INVENTION

This invention relates to the field of pharmacogenomics and specifically to the application of genetic polymorphisms to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Cancer chemotherapy is limited by the predisposition of specific populations to drug toxicity or poor drug response. Thus, for example, pharmacogenetics (the effect of genetic differences on drug response) has been applied in cancer chemotherapy to understand the significant inter-individual variations in responses and toxicities to the administration of anti-cancer drugs, which may be due to genetic alterations in drug metabolizing enzymes or receptor expression. For a review of the use of germline polymorphisms in clinical oncology, see Lenz, H. J. (2004) J. Clin. Oncol. 22(13):2519-2521; Park, D. J. et al. (2006) Curr. Opin. Pharma. 6(4):337-344; Zhang, W. et al. (2006) Pharma. and Genomics 16(7):475-483 and U.S. Patent Publ. No. 2006/0115827. For a review of pharmacogenetics and pharmacogenomics in therapeutic antibody development for the treatment of cancer, see Yan and Beckman (2005) Biotechniques 39:565-568.

Voltage-gated Sodium Channel (VGSC) is a large, multimeric complex, composed of an α subunit and one or more smaller β subunits. VGSC activity has been shown to contribute to many cellular behaviors integral to metastases, invasion and progression. In vitro and in vivo models have indicated that an increase in VGSC alpha gene expression is associated with metastatic potential, proliferation and progression of breast and prostate cancers.

Thymidylate synthase (TS), dihydropyrimidine dehydrogenase (DPD), and thymidine phosphorylase (TP) are important regulatory enzymes involved in the metabolism of the chemotherapeutic drug 5-Fluorouracil (5-FU).

Cell cycle regulation provides the foundation for a critical balance between proliferation and cell death, which are important factors in cancer progression. For example, a tumor suppressor gene such as p53 grants the injured cell time to repair its damaged DNA by inducing cell cycle arrest before reinitiating replicative DNA synthesis and/or mitosis (Kastan (1991) Cancer Res. 51:6304). More importantly, when p53 is activated based on DNA damage or other activating factors, it can initiate downstream events leading to apoptosis (Levine (1992) N. Engl. J. Med. 326:1350). The advent of tumor recurrence after radiation therapy depends significantly on how the cell responds to the induced DNA damage; that is, increased p53 function should induce apoptosis in the irradiated cell and thereby prevent proliferation of cancerous cells, whereas decreased p53 function may decrease apoptotic rates.

Finally, DNA repair capacity contributes significantly to the cell's response to chemoradiation treatment (Yanagisawa (1998) Oral Oncol. 34:524). Patient variability in sensitivity to radiotherapy can be attributed to either the amount of damage induced upon radiation exposure or the cell's ability to tolerate and repair the damage (Nunez (1996) Rad. One. 39:155). Irradiation can damage DNA directly or indirectly via reactive oxygen species, and the cell has several pathways to repair DNA damage including double-stranded break repair (DSBR), nucleotide excision repair (NER), and base excision repair (BER). An increased ability to repair direct and indirect damage caused by radiation will inherently lower treatment capability and hence may lead to an increase in tumor recurrence. Genes associated with DNA repair include XRCC1 and ERCC2.

Colorectal cancer (CRC) represents the second leading lethal malignancy in the USA. In 2005, an estimated 145,290 new cases will be diagnosed and 56,290 deaths will occur (Jemal, A. et al. (2005) Cancer J. Clin. 55:10-30). Despite advances in the treatment of colorectal cancer, the five year survival rate for metastatic colon cancer is still low, with a median survival of 18-21 months (Douglass, H. O. et al. (1986) N. Eng. J. Med. 315:1294-1295). Accordingly, it is desirable to provide a reliable screening method capable of predicting the clinical outcome of a specific therapeutic regime for treating CRC and other gastrointestinal cancers.

DESCRIPTION OF THE EMBODIMENTS

This invention provides methods to detect and correlate VGSC polymorphisms that have been determined to be clinically relevant to the treatment of gastrointestinal (GI) cancers.

One aspect of the invention provides for a method for identifying a patient suffering from a gastrointestinal cancer that is suitably treated by a therapy comprising the administration of one or more of a fluoropyrimidine drug, a topoisomerase inhibitor or a platinum drug. The method comprises screening a suitable sample isolated from the patient for a gene of interest that includes the genetic polymorphism SCN1A T1067A SNP T/T present in the VGSC gene. The presence of the polymorphism identifies the patient as being suitable for the therapy because a correlation between the presence of the polymorphism and a positive clinical response has been demonstrated by Applicant.

The therapy comprises administration of at least one of a fluoropyrimidine anti-cancer drug, a platinum drug or a topoisomerase inhibitor. In one embodiment, the method further comprises administration of an effective amount of one or more of these drugs to patients that have been selected as suitable for the chemotherapy. In one aspect, the therapy comprises administration of at least one of 5-FU, oxaliplatin or irinotecan. In another embodiment, the therapy is at least one of an equivalent of 5-FU, oxaliplatin or irinotecan. In a further aspect, at least two of the three are combined. In a further aspect, all three are combined in the treatment protocol.

The patient sample is isolated from a patient suffering from a gastrointestinal cancer which includes, but is not limited to rectal cancer, colorectal cancer, colon cancer, gastric cancer, lung cancer, non-small cell lung cancer (NSCLC) and esophageal cancer.

Another aspect of the invention provides a method for identifying a patient suffering from a gastrointestinal cancer that is at risk for side effects from a therapy comprising screening a suitable sample isolated from the patient for the genetic polymorphism SCN1A T1067A SNP T/T that may or may not be present in the VGSC gene. The presence of the polymorphism identifies the patient as being at a reduced risk for side effects. In one embodiment, the side effect is toxicity.

After a patient has been identified as suitable for the identified therapy, the invention further provides administration of an effective amount of at least one of a fluoropyrimidine drug, a platinum drug, or a topoisomerase inhibitor to the patient. In one embodiment, the therapy comprises administration of at least one of 5-FU, oxaliplatin or irinotecan. In another embodiment, the therapy is at least one of an equivalent of 5-FU, oxaliplatin or irinotecan.

The suitable sample used in the above described methods is at least one of a tumor sample, a sample of normal tissue corresponding to the tumor sample and a peripheral blood lymphocyte.

In yet a further aspect, the invention provides a kit for amplifying and/or for determining the molecular structure of at least a portion of the gene of interest, comprising a probe or primer capable of detecting the gene of interest and instructions for use. In one embodiment, the probe or primer is capable of detecting a polymorph in the gene of interest.

It will be appreciated by one of skill in the art that the embodiments summarized above may be used together in any suitable combination to generate additional embodiments not expressly recited above, and that such embodiments are considered to be part of the present invention.

MODES FOR CARRYING OUT THE INVENTION

The present invention provides methods and kits for determining a patient's likely response to specific cancer treatment by determining the patient's genotype at a gene of interest. Other aspects of the invention are described below or will be apparent to one of skill in the art in light of the present disclosure.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook et al. MOLECULAR CLONING: A LABORATORY MANUAL, 2$^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc., N.Y.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); ANIMAL CELL CULTURE (R. I. Freshney ed. (1987)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); TRANSCRIPTION AND TRANSLATION (B. D. Hames & S. J. Higgins eds. (1984)): IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); IMMUNOCHEMICAL METHODS IN CELL AND MOLECULAR BIOLOGY (Mayer and Walker, eds., Academic Press, London (1987)); HANDBOOK OF EXPERIMENTAL IMMUNOLOGY, Volumes I-IV (D. M. Weir and C. C. Blackwell, eds. (1986)): MANIPULATING THE MOUSE EMBRYO (Cold Spring Harbor Laboratory Press, Cold Spring Harbor, N.Y. (1986)).

Definitions

As used herein, certain terms may have the following defined meanings. As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extrachromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

A "gene of interest" or "polymorphism of interest" as used herein intends at least one or more of the 13 VGSC genes polymorphisms identified in the experimental section below. The polymorphisms in the genes of interest include SCN1A, 1B, 1A1, 1A2, 1A3, 1A4, 1A5, 1A_A3169G_SNP, 1A_C1702T_Nonsense Mutation, 1A_T1067A_SNP, 1A_C3637T_SNP, SCN8A_Ref_SNP_303802.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous to that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to a patient sample, nucleic acids, such as DNA or RNA, refers to cells, tissues or molecules separated from other DNAs or RNAs, respectively, that are present in the natural source. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytosine", "guanidine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

The term "treating" as used herein is intended to encompass curing as well as ameliorating at least one symptom of the condition or disease. For example, in the case of cancer, treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7):1404-1411.

A "response" shall mean a 50% reduction in tumor.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

"Non-response" (NR) to a therapy defines patients whose evidence of disease has remained constant or has progressed.

"Time to tumor progression" is the time between treatment and initial response and the time when resistance to initial treatment or loss of treatment efficacy.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to treat a gastrointestinal cancer.

The compounds can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

This invention provides a method for selecting a therapeutic regimen or determining if a certain therapeutic regimen is more likely to treat a GI cancer or if it is the appropriate chemotherapy for that patient as compared to other available chemotherapies. In one embodiment, the method comprises detecting a polymorphism of interest that Applicant has shown to be clinically relevant in cancer treatment and prognosis. Clinical relevance includes, but is not specifically limited to, patient response to a particular therapy (for example, different chemotherapeutic regimes, or chemotherapy versus antibody therapy), likelihood of tumor recurrence, time to progression of tumor, survival, sensitivity, and toxicity.

In one embodiment, the method comprises determining the presence or absence of an allelic variant of a predetermined gene. In another embodiment, the method comprises determining the identity of a nucleotide of a predetermined allelic variant.

Determination of polymorphisms is well within the knowledge of one of skill in the art and is described further below.

In one aspect, the GI cancer comprises a cancer or neoplasm that is treatable by use of one or more of platinum-based therapy (oxaliplatin, cisplatin, carboplatin), fluoropyrimidine-based therapy (5-fluorouracil (5-FU), floxuriden (FUDR) capecitabine, UFT), irinotecan (CP-11), radiation and surgical resection. Non-limiting examples of gastrointestinal cancers include, but are not limited to, rectal cancer, colorectal cancer, colon cancer, gastric cancer, lung cancer, non-small cell lung cancer (NSCLC), and esophageal cancer. In a preferred aspect of the invention, the cancer comprises advanced colorectal cancer (CRC) that is treatable with a topoisomerase inhibitor, a fluoropyrimidine drug and a platinum drug, or their equivalents, or combinations thereof. In one aspect, embodiment, the fluoropyrimidine drug is 5-FU, the platinum drug is oxaliplatin, and the topoisomerase inhibitor is irinotecan.

In one embodiment, the chemotherapeutic regimen further comprises radiation therapy. In an alternate embodiment, the therapy comprises administration of an anti-VEGF such as Arastin (Genentech) antibody or biological equivalent thereof.

Genetic polymorphisms in DNA repair and drug metabolism pathways have been shown to be associated with efficacy and toxicity in patients with metastatic colon cancer treated with 5-fluorouracil and oxaliplatin. Recent studies have demonstrated in in vitro models that the neurotoxicity associated with oxaliplatin may be linked to an effect on neuronal voltage-gated sodium channels (VGSC) (Grolleau et al. (2001) J. Neurophysiology 85:2293-2297). In vitro and in vivo models showed that increased VGSC alpha gene expression was associated with metastatic potential, proliferation and progression of breast and prostate cancer indicating a role in predicting toxicity and efficacy to chemotherapy. However, there are no reported studies pertaining to whether VGSC gene polymorphisms may predict clinical outcome in a phase II study of combination oxaliplatin with 5-FU in patients with colorectal cancer refractory to 5-FU and/or irinotecan based chemotherapy (Rougier P. and Lepre C. (2005) Semin. Oncol. 32(6 Suppl. 8):15-20).

FU (5-fluorouracil) is an antimetabolite drug that has been in use for over four decades. It targets thymidylate synthase and the enzyme dihydropyrimidine dehydrogenase (DPD). Several derivatives and substitutes for 5-FU and their use in gastric cancer have been reported in Ajani (2005) The Oncologist 10 (suppl.3):49-58. It is often used in combination with the platinum drug oxaliplatin and irinotecan.

Oxaliplatin is a relatively new diamine cyclohexane platinum derivative that is active in several solid tumor types, especially in some cisplatin/carboplatin refractory diseases such as colorectal cancer (Machover et al. (1996) Ann. Oncol. 7:95-98) and is reported to be better tolerated than cisplatin, especially in terms of renal toxicity (Grolleau, F. et al. (2001) supra).

Irinotecan belongs to a general group of chemotherapy drugs known as topoisomerase inhibitors. It is sold under the trade names Camptosar, Camptothecan-11 and CPT-11. It is believed to act by stopping the growth of cancer by preventing cell division.

The Applicant has determined that the presence of specific VGSC gene polymorphisms in the cells of GI cancer patients treated with a combination therapy of 5-FU, oxaliplatin, and irinotecan correlates to an increase in overall survival rate.

Accordingly, one aspect of the invention provides a method for identifying a gastrointestinal cancer patient that is suitably treated by a pre-selected therapy comprising screening a suitable sample isolated from the patient for the genetic polymorphism SCN1A T1067A SNP T/T present in the VGSC gene. The presence of the polymorphism identifies the patient as being suitable for the therapy.

The methods of the invention are applicable to therapies comprising administration of at least one of a fluoropyrimidine drug, or equivalent thereof, a platinum drug, or equivalent thereof, or a topoisomerase inhibitor or equivalent thereof. In one embodiment, the therapy comprises combinations of at least two of these drugs. In another embodiment, the therapy comprises combinations of all three of these drugs. In a specific embodiment, the therapy comprises administration of 5-FU, oxaliplatin, and irinotecan.

In one embodiment, the sample to be screened is the tumor tissue itself or normal tissue immediately adjacent to the tumor. In a further embodiment, the sample is of normal tissue corresponding to the tumor sample. In yet a further embodiment, any cell expected to carry the gene of interest, when the polymorphism is genetic, such as a peripheral blood lymphocyte isolated from the patient, is a suitable cell or tissue sample.

Diagnostic Methods

The invention further features predictive medicines, which are based, at least in part, on determination of the identity of the polymorphic region of the gene of interest.

For example, information obtained using the diagnostic assays described herein is useful for determining if a patient will respond to cancer treatment of a given type. Based on the prognostic information, a doctor can recommend a regimen or therapeutic protocol, useful for treating cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup specific; and 3) an accelerated and less costly development for drug candidates and more optimal drug labeling.

The polymorphism of interest can be identified using the methods exemplified below or any other of the various methods known to those skilled in the art. Art known methods include without limitation DNA microarray technology that also has many varieties, e.g., DNA chip devices and systems high-density microarrays for high-throughput screening applications and lower-density microarrays. Methods for microarray fabrication are known in the art and include various inkjet and microjet deposition or spotting technologies and processes, in situ or on-chip photolithographic oligonucleotide synthesis processes, and electronic DNA probe addressing processes. The DNA microarray hybridization applications has been successfully applied in the areas of gene expression analysis and genotyping for point mutations, single nucleotide polymorphisms (SNPs), and short tandem repeats (STRs). Additional methods include interference RNA microarrays and combinations of microarrays and other methods such as laser capture microdissection (LCM), comparative genomic hybridization (CGH) and chromatin immunoprecipitation (ChiP). For a review of these technologies, see He et al. (2007) Adv. Exp. Med. Biol. 593:117-133 and Heller (2002) Annu. Rev. Biomed. Eng. 4:129-153. Other art-known methods include, without limitation PCR, xMAP, invader assay, mass spectrometry, and pyrosequencing (Wang et al. (2007) 593:105-106). The patent literature also describes art known methods for SNP analysis.

Identification of the polymorph can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli, et al. (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert ((1997) PNAS USA 74:560) or Sanger (Sanger et al. (1977) PNAS USA 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO 94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl. Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732, entitled "Method of DNA Sequencing Employing A Mixed DNA-Polymer Chain Probe" and U.S. Pat. No. 5,571,676 entitled, "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA. DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc Natl. Acad. Sd USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 by of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) PNAS USA 86:6230 and Wallace et al. (1979) Nucl. Acids Res.

6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell Probes 6:1).

In another embodiment, identification of the allelic variant is carried out using an oligonucleotide ligation assay (OLA), as described, e.g., in U.S. Pat. No. 4,998,617 and in Laridegren, U. et al. Science 241:1077-1 080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996) Nucleic Acids Res. 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site (Cohen, D. et al. (French Patent 2,650,840; PCT Appln. No. WO 91/02087)). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C., et al. (1990) Genomics 8:684-692; Kuppuswamy, M. N. et al. (1991) Proc. Natl. Acad. Sci. (U.S.A.) 88:1143-1147; Prezant, T. R. et al. (1992) Hum. Mutat. 1:159-164; Ugozzoli, L. et al. (1992) GATA 9:107-112; Nyren, P. et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation.

Antibodies to the wild-type or signal peptide mutated forms of the signal peptide proteins can be prepared according to methods known in the art.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine clinical response to the preselected therapy.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO 91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo, G. J. (1992) "PCR In Situ Hybridization: Protocols And Applications", Raven Press, N.Y.).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S. and Kramer, F. R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis, L. G. (1998) Science 279:1228-9) as has the use of multiple beacons simultaneously (Marras, S. A. (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the polymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

Methods of Treatment

The invention further provides methods of treating subjects having cancer after they have been identified as suitable for combination therapy described herein by administering an effective amount of one or more of a fluoropyrimidine drug, a platinum drug, or a topoisomerase inhibitor, or equivalents thereof. In a preferred embodiment, the fluoropyrimidine drug is 5-FU, the platinum drug is oxaliplatin, and the topoisomerase inhibitor is irinotecan. In one embodiment, the method comprises (a) determining the identity of the allelic variant identified herein as relevant to sensitivity to 5-FU, oxaliplatin or irinotecan, or equivalents thereof; and (b) administering to the subject an effective amount of 5-FU, oxaliplatin or irinotecan, or equivalents thereof.

Kits

As set forth herein, the invention also provides diagnostic methods for determining the type of allelic variant of a polymorphic region present in the gene of interest. In some embodiments, the methods use probes or primers comprising nucleotide sequences which are complementary to the polymorphic region of the gene of interest. Accordingly, the invention provides kits for performing these methods.

In an embodiment, the invention provides a kit for determining whether a subject is likely to respond to a fluoropyrimidine drug, a platinum drug, or a topoisomerase inhibitor, or equivalents thereof based chemotherapy. In a preferred embodiment, the fluoropyrimidine drug is 5-FU, the platinum drug is oxaliplatin, and the topoisomerase inhibitor is irinotecan.

The kits contain one or more of the compositions described above and instructions for use. As an example only, the invention also provides kits for determining response to cancer treatment containing a first and a second oliqonucleotides specific for the polymorphic region of the gene of interest. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.

The invention now being generally described, it will be more readily understood by reference to the following examples which are included merely for purposes of illustration of certain aspects and embodiments of the present invention, and are not intended to limit the invention.

EXPERIMENTAL EXAMPLE

Methods: 152 patients were enrolled in this phase II study. 149 patients (male/female; 78/74, median age; 60). The dose of oxaliplatin was 130 mg/m$^2$ every 3 weeks and 5-FU was 200 mg/m$^2$/day CI for 10 weeks followed by 2 weeks rest. Thirteen (13) VGSC genes polymorphisms (SCN1A, 1B, 1A1, 1A2, 1A3, 1A4, 1A5, 1A_A3169G_SNP, 1A_C1702T_Nonsense Mutation, 1A_T1067A_SNP, 1A_C3637T_SNP, SCN8A_Ref_SNP__303802) were tested. Genomic DNA was extracted from peripheral blood samples and polymorphisms were analyzed by PCR-based RFLP technique using methods well known in the art.

Primers to identify the polymorphism are:

```
Forward (TGCACAAAGGAGTAGCTTATG)       (SEQ ID NO: 1)
and,

Reverse (AGTCAAGATCTTTCCCAATTTCAG).  (SEQ ID NO: 2)
```

Results: Patients with SCN1A_T1067A_SNP T/T genotype showed a significant better response rate (p=0.02, 21.9% [23/105] versus 11.3% [5/44]), time to tumor progression (TTP) (p=0.02, 4.6 months vs. 3.4 months), overall survival (p<0.001, 12.3 months. vs. 8.0 months.), and frequency of grade 3-4 toxicities (p=0.002) compare to patients with T/A genotype. No A/A genotype was observed.

Conclusions: VGSC activity has been shown to contribute to many cellular behaviors integral to metastases, invasion and progression its cellular/molecular basis remains unknown. VGSC gene polymorphism is a useful molecular marker for survival and toxicity in patients with colorectal cancer treated with oxaliplatin/5-FU.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

I claim:

1. A method for selecting or not selecting a therapy comprising administration of 5-Fluorouracil and/or oxaliplatin for a colorectal cancer patient, comprising screening a suitable sample isolated from the colorectal cancer patient for the SCN1A T1067A SNP genetic polymorphism in the Voltage-gated Sodium Channel (VGSC) gene, and selecting the therapy for the patient if a SCN1A T1067A T/T genotype is present in the sample, or not selecting the therapy for the patient if a SCN1A T1067A T/A genotype is present in the sample.

2. The method of claim 1, wherein the therapy comprises administration of 5-Fluorouracil and oxaliplatin.

3. The method of claim 1, wherein the suitable sample is at least one of a tumor sample, a sample of normal tissue corresponding to the tumor sample, or a peripheral blood lymphocyte.

4. The method of claim 1, wherein the polymorphism is screened with a method selected comprising DNA microarray, PCR or sequencing.

5. The method of claim 1, further comprising administering the therapy to the patient selected for the therapy.

6. The method of claim 5, wherein the therapy consists essentially of 5-Fluorouracil and oxaliplatin.

7. The method of claim 5, wherein the therapy consists essentially of 5-Fluorouracil and oxaliplatin.

* * * * *